United States Patent
Xiu et al.

(10) Patent No.: US 7,528,210 B2
(45) Date of Patent: *May 5, 2009

(54) METHOD OF PURIFICATION OF DIHYDRIC PHENOLS

(75) Inventors: Guohua Xiu, Shanghai (CN); Tong Sun, Pudong (CN); Jan Plen Lens, Breda (NL); Sunil Ashtekar, Karnataka (IN); Mahesh Malusare, Karnataka (IN); Gurram Kishan, Karnataka (IN); Pushpa Narayanan, Karnataka (IN)

(73) Assignee: SABIC Innovative Plastics IP B.V., Bergen op Zoom (NL)

( * ) Notice: Subject to any disclaimer, the term of this patent is extended or adjusted under 35 U.S.C. 154(b) by 279 days.

This patent is subject to a terminal disclaimer.

(21) Appl. No.: 11/277,956

(22) Filed: Mar. 30, 2006

(65) Prior Publication Data

US 2007/0232774 A1    Oct. 4, 2007

(51) Int. Cl.
*C08G 63/00*    (2006.01)
*C08G 63/02*    (2006.01)

(52) U.S. Cl. ............ 528/176; 528/190; 528/193; 562/485; 562/486; 562/600; 568/637; 568/749; 568/750

(58) Field of Classification Search .......... 528/176, 528/190, 193; 562/485, 486, 600; 568/637, 568/749, 750

See application file for complete search history.

(56) References Cited

U.S. PATENT DOCUMENTS

| | | | |
|---|---|---|---|
| 3,351,669 | A | 11/1967 | Anderson et al. |
| 5,436,359 | A | 7/1995 | Masuya et al. |
| 5,675,021 | A | 10/1997 | Eggeman et al. |
| 5,811,538 | A | 9/1998 | Riley et al. |
| 6,417,346 | B1 | 7/2002 | Salome et al. |
| 6,525,226 | B2 | 2/2003 | Choudhary et al. |
| 6,548,722 | B1 | 4/2003 | Choudhary et al. |
| 6,554,967 | B1 | 4/2003 | Tanaka et al. |
| 6,716,510 | B2 * | 4/2004 | Tomioka et al. ............ 428/64.7 |
| 6,962,967 | B2 | 11/2005 | Peters et al. |
| 2003/0018219 | A1 | 1/2003 | Choudhary et al. |
| 2005/0222380 | A1 | 10/2005 | Peters et al. |
| 2007/0232775 | A1 * | 10/2007 | Ashtekar et al. ............ 528/86 |

FOREIGN PATENT DOCUMENTS

| | | |
|---|---|---|
| GB | 1357280 A | 6/1974 |
| GB | 1426769 A | 3/1976 |
| JP | 2000159715 A2 | 6/2000 |
| JP | 2004016897 A2 | 1/2004 |
| JP | 2005053845 A2 | 3/2005 |
| WO | WO 03011865 A1 | 2/2003 |
| WO | WO 2004096747 A1 | 11/2004 |
| WO | WO 2005007667 A1 | 1/2005 |
| WO | WO 2005035468 A1 | 4/2005 |
| WO | WO 2005108400 A1 | 11/2005 |

OTHER PUBLICATIONS

Sci-Tech Encyclopedia McGraw-Hill Encyclopedia of Science and Technology, 5th edition, published by The McGraw-Hill Companies, Inc. 2008.*
PCT International Search Report for International Application No. PCT/US2007/005661, filed Mar. 5, 2007.
Peric, J. et al., "Removal of zinc, copper and lead by natural zeolite-a comparison of adsorption isotherms". Water Research, Elsevier, Amsterdam, NL, vol. 38, No. 7, Apr. 2004, pp. 1893-1899.

* cited by examiner

*Primary Examiner*—Terressa M Boykin

(57) ABSTRACT

A process comprising the steps of dissolving a dihydric phenol in a solvent to form a solution A; contacting the solution A with a zeolite; filtering the zeolite to form a solution B; adding an anti-solvent to the solution B to form a solution C; and distilling the solution C; wherein the dihydric phenol is represented by Formula (I):

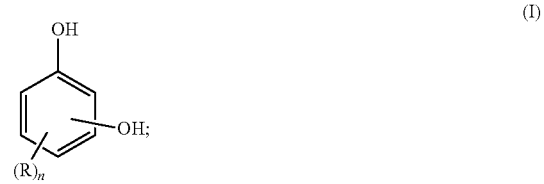

wherein R is a hydrogen atom or an aliphatic functionality having 1 to 6 carbon atoms and n is an integer having a value 1 to 4.

19 Claims, No Drawings

METHOD OF PURIFICATION OF DIHYDRIC PHENOLS

BACKGROUND

This disclosure generally relates to a method for the purification of dihydric phenols. More particularly the disclosure relates to a method for the purification of methyl hydroquinone.

The present method of preparing dihydric phenols involves oxidation of the corresponding aromatic amines to benzoquinones followed by the reduction of the benzoquinones to hydroquinones. For example, the commercial process for the preparation of methyl hydroquinone employs o-toluidine as the raw material. The acid sulfate of o-toluidine is prepared by sulfuric acid treatment and is oxidized with manganese dioxide and sulfuric acid at lower temperatures of about 5° C. to about 8° C. The methyl benzoquinone formed is then steam distilled and reduced in the presence of zinc and/or iron and acid to form methyl hydroquinone. The isolated methyl hydroquinone has a typical purity of 99 percent and typically contains about 30 parts per million (ppm) to about 50 ppm of metals like iron, manganese, sodium, zinc, calcium and others as impurities. One of the main uses of methyl hydroquinone is in the preparation of co-polymers having good chemical resistance properties.

Methyl hydroquinone can be used in the preparation of co-polymers such as polycarbonates and polyesters. The presence of the metal residues in methyl hydroquinone in ppm levels considerably affects the properties of the co-polymer, such as for example, a reduced molecular weight buildup, reduced transparency, and an increase in color. This is true especially for dihydroxy based co-polymers and especially BPA containing PC. It is believed that metal ions present even in ppm levels, especially the transition metals like iron, can give rise to color formation during polymerization and further processing at high temperatures by forming colored metal complexes as by-products. Further, side reactions such as Fries rearrangement, which is known to be catalyzed by metals, can also occur during the polymerization.

Hence there is a need for a better purification technique that will help to reduce the metal ion concentration in the dihydric phenol to an amount such that the residual metal ion or ions will not interfere with the properties of the co-polymer prepared using the purified dihydric phenol.

BRIEF SUMMARY

Disclosed herein is a process for the purification of dihydric phenols. In one embodiment, the process comprises the steps of dissolving the dihydric phenol in a solvent to form a solution A; contacting the solution A with a zeolite; filtering the zeolite to form a solution B; adding an anti-solvent to the solution B to form a solution C; and distilling the solution C; wherein the dihydric phenol is represented by Formula (I):

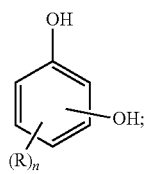

(I)

wherein R is a hydrogen atom or an aliphatic functionality having 1 to 6 carbon atoms and n is an integer having a value of 1 to 4.

In another embodiment, the process comprises the steps of dissolving the dihydric phenol in a mixture of a solvent and an anti-solvent to form a solution A; contacting the solution A with a zeolite; filtering the zeolite to form a solution B; and distilling the solution B; wherein the dihydric phenol is represented by Formula (I):

(I)

wherein R is a hydrogen atom or an aliphatic functionality having 1 to 6 carbon atoms and n is an integer having a value 1 to 4.

The disclosure may be understood more readily by reference to the following detailed description of the various features of the disclosure and the examples included therein.

DETAILED DESCRIPTION

Disclosed herein is a process for the purification of dihydric phenols. Dihydric phenols are generally useful as monomers or co-monomers in the preparation of polymers. Some dihydric phenols, for example methyl hydroquinone, are key monomers for preparing polycarbonates (PC) that are used in specialty applications, such as for example in packaging of cosmetic, perfume, or biochemical applications.

The singular forms "a", "an" and "the" include plural referents unless the context clearly dictates otherwise. All ranges disclosed herein are inclusive of the recited endpoint and independently combinable (for example ranges of "from about 2 grams to about 10 grams" is inclusive of the endpoints and all the intermediate values of the ranges of 2 grams to about 10 grams).

The modifier "about" used in connection with a quantity is inclusive of the stated value and has the meaning dictated by the context (for example, includes the degree of error associated with measurement of the particular quantity).

Compounds are described using standard nomenclature. For example, any position not substituted by any indicated group is understood to have its valency filled by a bond as indicated, or a hydrogen atom. A dash ("—") that is not between two letters or symbols is used to indicate a point of attachment for a substituent. For example, —CHO is attached through carbon of the carbonyl group.

As used herein the term "aliphatic functionality" refers to an organic functionality having at least one carbon, a valence of at least one consisting of a linear or branched array of atoms that is not cyclic. Exemplary aliphatic functionalities include, but are not limited to methyl, ethyl, propyl, isopropyl, butyl, isobutyl, pentyl and isopentyl groups.

Disclosed herein is a process for the purification of dihydric phenols. The purification process results in a reduction in the metal ion concentration of iron (Fe), zinc (Zn), sodium (Na), calcium (Ca), manganese (Mn) and other metal ions that may be present in the unpurified dihydric phenols from ppm levels to parts per billion (ppb) levels. One process for the purification of the dihydric phenols of Formula (I) comprises the steps of dissolving the dihydric phenol in a solvent to form a solution A; contacting the solution A with a zeolite; filtering the zeolite to form a solution B; adding an anti-solvent to the solution B to form a solution C; and distilling the solution C.

In another embodiment, a process for the purification of the dihydric phenol of Formula (I) comprises, dissolving the dihydric phenol in a mixture of a solvent and an anti-solvent to form a solution A; contacting the solution A with a zeolite; filtering the zeolite to form a solution B; and distilling the solution B.

Non-limiting examples of the dihydric phenols of Formula (I) that can be purified using the processes disclosed herein include, but are not limited to, hydroquinone, resorcinol, catechol, 2-methyl-1,4-hydroquinone, 2,5-dimethyl-1,4-hydroquinone, 2-ethyl-1,4-hydroquinone, 2,5-diethyl-1,4-hydroquinone, 2-tertiarybutyl-1,4-hydroquinone, 2,3,5-trimethyl-1,4-hydroquinone, 2-isopropyl-1,4-hydroquinone, and 2,5-diisopropyl-1,4-hydroquinone. Mixtures of two or more of the foregoing dihydric phenols can also be purified.

Suitable solvents that can be employed for dissolving the dihydric phenol comprise water, ketones having 3 to 10 carbons, alcohols having 1 to 12 carbons, esters having 4 to 10 carbons or mixtures of the foregoing solvents. Specific, non-limiting examples of suitable solvents include acetone, methyl ethyl ketone, methyl isobutyl ketone, methyl butyl ketone, methyl propyl ketone, methyl alcohol, ethyl alcohol, isopropyl alcohol, butyl alcohol, isobutyl alcohol, isopentyl alcohol, n-pentyl alcohol, n-hexyl alcohol, ethyl acetate, butyl acetate, and a mixture of one or more of the foregoing solvents. A mixture having a suitable amount of water and one or more of the solvents listed above can also be used to dissolve the dihydric phenol. In one embodiment the solvent used is acetone.

The amount of the solvent used in the purification can be from about 0.5 grams to about 10 grams, per gram of the dihydric phenol. Within this range the amount may be greater than or equal to about 1 grams, or more specifically, greater than or equal to about 3 grams, per gram of the dihydric phenol. Also within this range the amount may be less than or equal to about 7 grams, or more specifically less than or equal to about 5 grams, per gram of the dihydric phenol.

Suitable anti-solvents used in the purification of the dihydric phenol include hydrocarbon solvents having 6 to 20 carbons. Examples of suitable anti-solvents include, but are not limited to, hexane, petroleum ether, toluene, xylene, and a mixture of one or more of the foregoing anti-solvents. In one embodiment, the anti-solvent used is toluene.

The amount of the anti-solvent used in the purification can be from about 0.1 grams to about 50 grams per gram of the dihydric phenol. Within this range the amount may be greater than or equal to about 3 grams, or more specifically, greater than or equal to about 10 grams, per gram of the dihydric phenol. Also within this range the amount may be less than or equal to about 25 grams, or more specifically less than or equal to about 20 grams, per gram of the dihydric phenol. It is to be noted that the solvent used in the purification process must have a lower boiling point than the boiling point of the anti-solvent. Specific non-limiting examples of solvent and anti-solvent combinations include, acetone and toluene; methyl ethyl ketone and toluene; methyl isobutyl ketone and toluene; and methyl isobutyl ketone and petroleum ether.

In one embodiment, where a mixture of a solvent and an anti-solvent is employed to dissolve the dihydric phenol, the combined amount of the solvent and the anti-solvent used in the purification can be about 0.6 grams to about 60 grams, per gram of the dihydric phenol. Within this range the amount may be greater than or equal to about 4 grams, or more specifically, greater than or equal to about 13 grams, per gram of the dihydric phenol. Also within this range the amount may be less than or equal to about 32 grams, or more specifically, less than or equal to about 25 grams, per gram of the dihydric phenol. Typically the amount of anti-solvent used is about 0.2 to 5 times the amount of the solvent used in the process. It is to be noted that to ensure complete dissolution of the dihydric phenol in the solvent or in the combination of the solvent and the anti-solvent, the dissolution step may be carried out at a temperature of about 25° C. to about 100° C. Within this range, the temperature may be greater than or equal to about 40° C., or more specifically, greater than or equal to about 50° C. Also within this range, the temperature may be less than or equal to about 90° C., or more specifically, less than or equal to about 80° C.

A variety of zeolites can be used in the purification process. Commercially available zeolites include both natural zeolites and synthetic zeolites. Both natural and synthetic zeolites are microporous crystalline aluminosilicates of Group IA and Group IIA elements such as sodium, magnesium, potassium and calcium, with well-defined structures. They are often also referred to as molecular sieves. They have a three-dimensional network structure (like a honeycomb structure). The basic structural units are tetrahedrons $[SiO_4]$-4 and $[AlO_4]$-5, where the silicon and aluminum atoms are placed centrally and larger oxygen atoms are placed at the corners of the tetrahedron. The metal atoms are coordinated with the four oxygen anions at the four corners of a tetrahedron, and the oxygen atoms are commonly shared by the tetrahedrons. The chemical composition of these zeolites in dehydrated form is expressed by the general Formula (III):

$$M_{2/m} \cdot Al_2O_3 \cdot nSiO_2 \qquad (III);$$

wherein M is the metal ion of an alkaline metal, such as for example sodium ion, potassium ion; or of an alkaline earth metal, such as for example calcium ion, magnesium ion, and barium ion; "m" is the valency of the corresponding metal and n is the mole ratio of silica ($SiO_2$) to alumina ($Al_2O_3$).

Specific non-limiting examples of zeolites include, molecular sieve Y-MS, molecular sieve 4A, molecular sieve 3A, molecular sieve CBV 901, molecular sieve beta zeolite, Zeolite H-Pentasil, Zeolite H-Modernite, MS PSA-H Zeolite SAPO-11; Zeolite ZSM-5 H-form, Zeolite ZSM-5 Na-form, clinoptilolite, chabazite, faujasite, mordenite, erionite, phillipsite, and laumontite. In one embodiment, the zeolite is clinoptilolite. Typically clinoptilolite has a silica to alumina ratio of 5 to 1.

In certain embodiments the amount of zeolite employed in the process for the purification of the dihydric phenols can be about 1 weight percent to about 300 weight percent, relative to an amount of the dihydric phenol. Within this range the amount may be greater than or equal to about 5 weight percent, or more specifically, greater than or equal to about 10 weight percent, relative to an amount of the dihydric phenol. Also within this range the amount may be less than or equal to about 225 weight percent, or more specifically less than or equal to about 150 weight percent, relative to an amount of the dihydric phenol.

As previously described, the solution A obtained is contacted with the zeolite to effect purification of the dihydric phenol. This step of contacting the solution A with the zeolite is carried out at a temperature of from about 25° C. to about 120° C. Within this range the temperature may be greater than or equal to about 40° C., or more specifically, greater than or equal to about 50° C. Also within this range the temperature may be less than or equal to about 110° C., or more specifically, less than or equal to about 80° C. The time taken for the purification of the dihydric phenol using zeolite can be about 0.1 hour to about 30 hours. Within this range the time may be greater than or equal to about 1 hour, or more specifically, greater than or equal to about 3 hours. Also within this range the time may be less than or equal to about 20 hours, or more specifically, less than or equal to about 10 hours.

Typically, the purified dihydric phenol is isolated by distilling the solution C. In one embodiment, isolation of the purified dihydric phenol can be achieved by partially distilling the lower boiling solvent from the solution C. The partial distillation of the solvent results in the precipitation of the purified dihydric phenol, and the remainder of the solvent present in the solution C helps to keep the color forming impurities in solution. The amount of solvent distilled is about 10 percent by weight to about 80 percent by weight, relative to the amount of the solvent employed for the dissolution of the impure dihydric phenol to form the solution A. Within this range, the amount of the solvent may be greater than or equal to about 30 percent by weight, or more specifically, greater than or equal to about 40 percent by weight, relative to the amount of the solvent used to form the solution A. Also within this range, the amount of the solvent may be less than or equal to about 70 percent by weight, or more specifically, less than or equal to about 50 percent by weight, relative to the amount of the solvent used to form the solution A. Alternately, when the dihydric phenol is dissolved in a mixture of the solvent and the anti-solvent, isolation of the purified dihydric phenol can be achieved by partially distilling the solvent from the solution B. The purification of the dihydric phenol can be carried out in a batch mode, continuous mode or in a semi-continuous mode as known to a person skilled in the art.

As previously discussed, one of the end uses of the purified dihydric phenols is in the preparation of polymers and co-polymers, for example, polycarbonates. The polymers and co-polymers comprise structural units derived from the dihydric phenols having Formula (I), where the structural units are represented by Formula (II):

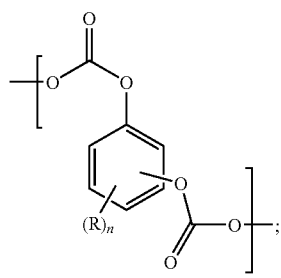

(II)

wherein R and n are as described previously. Suitable methods for the preparation of polycarbonates include, but are not limited to, interfacial polymerization and melt transesterification polymerization methods. In the interfacial polymerization method, the purified dihydric phenols of Formula (I) are reacted with phosgene to provide the polycarbonates. In melt-transesterification polymerization, the purified dihydric phenols are either homopolymerized, or co-polymerized with one or more bisphenols other than the dihydric phenols of Formula (I) in the presence of carbonate precursors, such as for example, diphenyl carbonate or bismethylsalicyl carbonate (bMSC). A catalyst is generally used to effect the trans-esterification reaction. Suitable examples of the catalysts include quaternary phosphonium salts, tetraalkylammonium salts, sodium hydroxide, or combinations of sodium hydroxide with the quaternary phosphonium salts or the tetraalkylammonium salts. The polymers or co-polymers prepared using the purified dihydric phenol show better molecular weight build up, increased transparency, and improved color, that is, a lower yellowness index (YI). The color improvement in the purified dihydric phenol can be measured in terms of the APHA value. The color improvement in the polymer prepared using the purified dihydric phenols can be measured in terms of YI.

The polymer or co-polymer prepared using the purified dihydric phenol can be used in various polymer compositions. The compositions may further optionally include various additives ordinarily incorporated in resin compositions of this type. Such additives may include antioxidants, heat stabilizers, flame retardants, UV stabilizers, anti-static agents (tetraalkylammonium benzene sulfonate salts, tetraalkylphosphonium benzene sulfonate salts, and the like), mold releasing agents (pentaerythritol tetrastearate, glycerol monostearate, and the like), and the like, and combinations comprising the foregoing. For example, the polymer composition can comprise a heat stabilizer from about 0.01 weight percent to about 0.1 weight percent; an antistatic agent from about 0.01 weight percent to about 1 weight percent; and/or a mold releasing agent from about 0.1 weight percent to about 1 weight percent, each based upon the total weight of the polymer.

The polymer compositions may be used for any application where desirable material properties, such as good physical properties, low color, and high transparency are required. In certain embodiments, the polymers may be used for packaging applications (especially for packaging drugs, cosmetics, perfumes, and biochemical materials), automotive parts, telecommunication accessories (for example, cell phone covers), computers and consumer electronics, construction materials, medical devices, eyewear products, secure documents including passports and ID cards, credit cards, films and sheets (including those used in display applications), and others.

A further understanding of the techniques described above can be obtained by reference to certain specific examples that are provided herein for purposes of illustration only and are not intended to be limiting.

EXAMPLES

The following examples illustrate processes by which dihydric phenols can be purified by using zeolite, thereby leading to a purified dihydric phenol having a reduced absorptivity in the visible range.

Methyl hydroquinone (MeHQ) used for purification in the following examples was obtained from commercial sources, such as, for example, Dalian in China, Shirdi chemicals in India and from Hunan in China, and is hereinafter referred to as raw MeHQ. The zeolite used for purifying the raw MeHQ includes natural clinoptilolite (particle size 1 to 3 millimeters (mm), from Dalian Liding Natural Products Co., Ltd.) and 4A molecular sieve zeolite (0.5 to 0.9 mm; from Shanghai Jinglong Chemical Co., Ltd.).

Inductively Coupled Plasma-Atomic Emission Spectrometer (ICP-AES) was used to measure the concentration of, sodium, potassium, calcium, iron, zinc, nickel, manganese, chromium and aluminum in ppm and ppb levels. The samples were analyzed using Spectro Ciros equipped with an ultrasonic nebulizer UT5000AT⁺. The sample used for analysis was prepared as follows. 10 grams of a sample of MeHQ (purified or unpurified MeHQ) was weighed in a platinum crucible and 2 ml of 50 percent aqueous sulphuric acid was added. The platinum crucible was then heated to about 650 C to char the sample. The residue obtained at the end was cooled to room temperature and treated with 2 ml of hydrochloric acid to form a solution. The solution was then transferred to a polypropylene container. The solution was then diluted to 50 ml with deionized water and sprayed into the ICP-AES for estimation of metal content.

APHA values were measured using a Macbeth Spectrophotometer using a 10 weight percent (weight by volume) solution of the purified dihydric phenol in acetonitrile (ACN).

Example 1 And Comparative Example-1 (CE-1)

200 grams (g) natural clinoptilolite (particle size 1 to 3 mm) was washed in distilled water till the washes obtained were clear. The washed clinoptilolite was then dried at 120° C. for 24 hours and the air in the clinoptilolite pores was replaced with ethyl acetate (EtAc) under vacuum, at a temperature of 40° C. This treated clinoptilolite was loaded into a reactor column which was previously filled with EtAc (the length of test section being 350 mm and its inner diameter 30 mm). A raw MeHQ-EtAC solution containing 28 weight percent of MeHQ (from Dalian, China) was prepared. The MeHQ-EtAc solution was contacted with the clinoptilolite loaded in the reactor column at a temperature of 30° C. The raw MeHQ-EtAc solution was fed from a high level tank into the column. A valve at the outlet of the column was used to adjust the flow rate to 0.5 to 1 milliliter/minute. Eluted samples were collected at 2 hour intervals and stored in separate glass bottles. The eluted samples were subjected to vacuum evaporation at a temperature of 45° C. to obtain concentrated MeHQ-EtAc. Then the concentrated MeHQ-EtAc solution, maintained at a temperature of 45° C., was poured into 200 milliliters (ml) reagent grade toluene, maintained at a temperature of −20° C. A precipitate of purified MeHQ was obtained. This was filtered, dried and analyzed for the metal ion concentration by inductively coupled plasma optical emission spectroscopy (ICP-AES). Table 1 includes the metal ion concentration (expressed in ppb levels) in the raw MeHQ and purified MeHQ. The general procedure described hereinabove was used with different zeolites as described below. Raw MeHQ obtained from commercial sources, was analyzed for the metal content, in CE-1 and the results are included in Table 1 below.

TABLE 1

| Example | Sample | Na | Mn | Fe | Zn | Ca |
|---|---|---|---|---|---|---|
| CE-1 | NA | 10250 | 410 | 4908 | 140 | 1151 |
| Example 1 | 2-3 hour sample | 670 | 0 | 180 | 110 | 660 |
|  | 4-5 hour sample | 820 | 0 | 60 | 30 | 630 |
|  | 6-7 hour sample | 330 | 0 | 90 | 30 | 740 |

NA—Not Applicable

Example 2

In this Example a similar method as used in Example 1 was followed for the purification of raw MeHQ, except that the natural clinoptilolite was treated with a 2 Molar solution of ammonium carbonate. The clinoptilolite was submerged for over 12 hours in the ammonium carbonate solution, washed with water and dried at 200° C. for 8 hours. This procedure was repeated again, before the clinoptilolite was used for the purification. The result on the removal of metal ions (concentrations expressed in ppb levels) from raw MeHQ is listed in Table 2 below.

TABLE 2

| Sample | Na | Mn | Fe | Zn | Ca |
|---|---|---|---|---|---|
| 2-3 hour sample | 707 | <100 | 108 | <100 | 981 |
| 4-5 hour sample | 687 | <100 | 65 | <100 | 755 |
| 6-7 hour sample | 732 | <100 | 44 | <100 | 147 |
| 8-9 hour sample | 770 | <100 | 74 | 655 | 624 |

Example 3

In this Example a similar method as used in Example 1 was followed for the purification of raw MeHQ, except that the natural clinoptilolite was replaced by 4A molecular sieve (MS; 0.5-0.9 mm; Shanghai Jinglong Chemical Co., Ltd.). The molecular sieve used was first washed with water and then dried at 400° C. for over 2 hours before being used for the purification. The result on the removal of metal ions (concentrations expressed in ppb levels) from raw MeHQ is listed in Table 3 below.

TABLE 3

| Sample | Na | Mn | Fe | Zn | Ca |
|---|---|---|---|---|---|
| 2-3 hour sample | 2334 | <100 | 91 | 75 | 1147 |
| 4-5 hour sample | 1193 | <100 | 16 | 195 | 1122 |
| 6-7 hour sample | 934 | <100 | 97 | 94 | 801 |
| 8-9 hour sample | 6603 | <100 | 214 | 122 | 860 |

Example 4

In this Example a similar method as used in Example 3 was followed for the purification of raw MeHQ, except that the molecular sieve 4A (MS; 0.5-0.9 mm; Shanghai Jinglong Chemical Co., Ltd.) was treated with a 2 Molar solution of ammonium carbonate. The molecular sieve was submerged for over 12 hours in the ammonium carbonate solution, washed with water and dried at 400° C. for 2 hours. This procedure was repeated again, before the molecular sieve was used for the purification. The result on the removal of metal ions from raw MeHQ is listed in Table 4 below.

TABLE 4

| Sample | Na | Mn | Fe | Zn | Ca |
|---|---|---|---|---|---|
| 2-3 hour sample | 1456 | <100 | 97 | 248 | 669 |
| 4-5 hour sample | 1411 | <100 | 167 | 133 | 653 |
| 6-7 hour sample | 2596 | <100 | 61 | 82 | 335 |
| 8-9 hour sample | 2623 | <100 | 213 | 270 | 1406 |

Effect of purification on the absorptivity of MeHQ:

The absorptivity of the purified sample for samples withdrawn at specific time intervals as described in Examples 1 to 4 above and the absorptivity of the raw MeHQ was measured at wavelengths of 440 nanometers (nm), 520 nm, and 759 nm. The absorptivity was measured using a Macbeth Spectrophotometer, using a 10 weight percent solution of MeHQ in acetonitrile (ACN). The absorptivity results are shown in Table 5 below.

TABLE 5

Absorptivity (milliliters/gram-centimeter)

| | Sample | | |
|---|---|---|---|
| | 440 nm | 520 nm | 750 nm |
| CE-1 | 0.06 | 0.042 | 0.023 |
| Example 1, 6-7 hour sample | 0.0087 | 0.0036 | 0.0036 |
| Example 2, 6-7 hour sample | 0.013 | 0.0057 | 0.0028 |
| Example 3, 6-7 hour sample | 0.0056 | 0.0016 | 0.0015 |
| Example 4, 6-7 hour sample | 0.0084 | 0.0031 | 0.0016 |

The results included in Tables 1 to 4 show that the natural clinoptilolite and the molecular sieves reduce the metal ion concentrations to parts per billion levels and also indicate a decrease in the absorptivity values in the visible range, as shown in the Table 5. Example 1 to 4 provide a continuous method for the purification of MeHQ.

Examples 5-6 And Comparative Example-2 (CE-2)

These Examples Provide A Batch Method For the Purification of MeHQ

The general procedure followed for purification is provided below. Raw MeHQ used in CE-2 (50 g), acetone (38 ml) and toluene (200 ml) were charged into a one-liter round bottom flask equipped with a condenser and a nitrogen blanket. The flask was then heated in an oil bath at 90° C. for about 30 to 45 minutes until all the raw MeHQ was dissolved. After complete dissolution of the raw MeHQ, the zeolite was added, and the resultant mixture was stirred at 90° C. at about 200 revolutions per minute for about 2 hours. The mixture was then filtered, and the filtrate was concentrated at 70° C. under a reduced pressure of 300 millibar. The pressure was slowly reduced to 175 millibar resulting in the precipitation of purified MeHQ. The mixture was then maintained at 5° C. for about 24 hours, and filtered and washed with 100 milliliters of toluene. The purified MeHQ was then dried, and the sample analyzed for ICP trace metal analysis, HPLC purity and APHA value. The isolated yield of the purified MeHQ was 90 percent of the theoretical yield. The results obtained for different zeolites is provided in Table 6 below. Raw MeHQ obtained from commercial sources, was analyzed for the metal content, in CE-2 and the results are included in Table 6 below.

TABLE 6

| Example No. | Zeolite | Zeolite weight percent based on a relative amount of raw MeHQ | Fe | Na | Zn | Mn | Ca | APHA |
|---|---|---|---|---|---|---|---|---|
| CE-2 | No Zeolite | 0 | 21441 | 25522 | 58624 | 13805 | 1407 | 139 |
| 5 | Clinoptilolite | 10 | 356 | 320 | 237 | <10 | 242 | 24 |
| 6 | ZSM-5 | 10 | 460 | 683 | 528 | 21 | 253 | 28 |

The results included in Table 6 show that the zeolites reduce the metal ion concentrations to parts per billion levels and also indicate a decrease in the APHA values.

While typical embodiments have been set forth for the purpose of illustration, the foregoing descriptions should not be deemed to be a limitation on the scope herein. Accordingly, various modifications, adaptations, and alternatives may occur to one skilled in the art without departing from the spirit and scope herein.

What is claimed is:

1. A method for purifying a dihydric phenol, the method comprising:

dissolving a dihydric phenol having Formula (I)

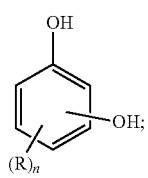

(I)

wherein R is a hydrogen atom or an aliphatic functionality having 1 to 6 carbon atoms; and n is an integer having a value of 1 to 4, in a solvent to form a solution A;

contacting the solution A with a zeolite wherein the step of contacting of the dihydric phenol in the solvent is carried out at a temperature of about 25° C. to about 120° C.;

filtering the zeolite to form a solution B;

adding an anti-solvent to the solution B to form a solution C, wherein the anti-solvent has a higher boiling point than the solvent; and distilling the solution C.

2. The method of claim 1, further comprising isolating the purified dihydric phenol.

3. A method for purifying a dihydric phenol, the method comprising: dissolving a dihydric phenol having Formula (I)

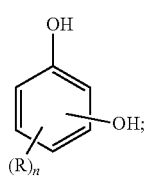

(I)

wherein R is a hydrogen atom or an aliphatic functionality having 1 to 6 carbon atoms; and n is an integer having a value of 1 to 4, in a mixture of a solvent and an anti-solvent to form a solution A, wherein the anti-solvent has a higher boiling point than the solvent;

contacting the solution A with a zeolite wherein the step of contacting of the dihydric phenol in the solvent is carried out at a temperature of about 25° C. to about 120° C.;

filtering the zeolite to form a solution B; and
distilling the solution B.

4. The method of claim 3, further comprising isolating the purified dihydric phenol.

5. The method of claim 1, wherein the dihydric phenol is 2-methyl-1,4-hydroquinone.

6. The method of claim 1, wherein the solvent comprises water, ketones having 3 to 10 carbons, alcohol having 1 to 12 carbons, esters having 4 to 10 carbons; or mixtures of one or more of the foregoing solvents.

7. The method of claim 1, wherein the solvent comprises ethylacetate or acetone.

8. The method of claim 1, wherein the anti-solvent comprises hydrocarbon solvents having 6 to 20 carbons.

9. The method of claim 1, wherein the anti-solvent comprises toluene.

10. The method of claim 1, wherein the adsorbent is present in an amount of about 1 percent by weight to about 300 percent by weight, relative to an amount of the dihydric phenol.

11. The method of claim 1, wherein the solvent is present in an amount of about 0.5 grams to about 10 grams, per gram of the dihydric phenol.

12. The method of claim 1, wherein the anti-solvent is present in an amount of about 0.1 grams to about 50 grams, per gram of the dihydric phenol.

13. The method of claim 3, wherein the adsorbent is present in an amount of about 1 percent by weight to about 300 percent by weight, relative to an amount of the dihydric phenol.

14. The method of claim 3, wherein the solvent is present in an amount of about 0.5 grams to about 10 grams, per gram of the dihydric phenol.

15. The method of claim 3, wherein the anti-solvent is present in an amount of about 0.1 grams to about 50 grams, per gram of the dihydric phenol.

16. A purified dihydric phenol prepared in accordance with the method of claim 1.

17. A polymer comprising structural units derived from the purified dihydric phenol of claim 16.

18. A purified dihydric phenol prepared in accordance with the method of claim 3.

19. A polymer comprising structural units derived from the purified dihydric phenol of claim 18.

* * * * *